(12) United States Patent
Bailey et al.

(10) Patent No.: US 7,524,379 B2
(45) Date of Patent: *Apr. 28, 2009

(54) MELT PROCESSABLE STARCH COMPOSITIONS

(75) Inventors: Valerie Ann Bailey, Florence, KY (US); Larry Neil Mackey, Fairfield, OH (US); Paul Dennis Trokhan, Hamilton, OH (US)

(73) Assignee: The Procter + Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/738,745

(22) Filed: Dec. 17, 2003

(65) Prior Publication Data
US 2004/0132873 A1    Jul. 8, 2004

Related U.S. Application Data

(63) Continuation of application No. 09/914,965, filed as application No. PCT/IB00/00233 on Mar. 7, 2000, now Pat. No. 6,709,526, which is a continuation-in-part of application No. 09/264,401, filed on Mar. 8, 1999, now abandoned.

(51) Int. Cl.
| | |
|---|---|
| C13F 3/00 | (2006.01) |
| C08B 31/00 | (2006.01) |
| C08B 33/00 | (2006.01) |
| C08G 61/02 | (2006.01) |
| C08J 3/00 | (2006.01) |
| C08K 7/00 | (2006.01) |
| C08L 3/00 | (2006.01) |
| C08L 89/00 | (2006.01) |
| D21H 19/54 | (2006.01) |
| A23B 7/10 | (2006.01) |
| A23F 3/00 | (2006.01) |
| A23K 1/00 | (2006.01) |
| A23L 1/05 | (2006.01) |
| A23L 1/22 | (2006.01) |
| A23L 1/216 | (2006.01) |
| A23L 1/40 | (2006.01) |
| A23L 1/238 | (2006.01) |
| A21D 10/00 | (2006.01) |
| A21D 13/00 | (2006.01) |

(52) U.S. Cl. ............................ 127/29; 536/102; 523/1; 523/220; 524/47; 426/49; 426/96; 426/549; 426/578; 426/589; 426/661

(58) Field of Classification Search .................. 127/29; 536/102; 523/1, 220; 524/47; 428/373; 426/49, 96, 549, 578, 589, 661
See application file for complete search history.

(56) References Cited

U.S. PATENT DOCUMENTS 1,856,401 A    5/1932    Prince (Continued)

FOREIGN PATENT DOCUMENTS

EP    0 108 364 B1    8/1986

(Continued)

OTHER PUBLICATIONS

"An experimental study of food melt rheology. I. Shear viscosity using a slit die viscometer and a capillary rheometer," A Senouci and A. C. Smith. Rheologica Acta 27 (1988), pp. 546-554.*

(Continued)

Primary Examiner—Patricia L Hailey
(74) Attorney, Agent, or Firm—C. Brant Cook

(57) ABSTRACT

The present invention relates to a starch composition comprising starch, a polymer that is substantially compatible with starch and has a weight-average molecular weight of at least 500,000 such that the polymer forms effective entanglements or associations with neighboring starch molecules, and preferably at least one additive to improve melt flow and melt processability. The additive may be a hydroxyl plasticizer, a hydroxyl-free plasticizer, a diluent, or mixtures thereof. The composition is melt processable on conventional thermoplastic equipment. The composition is especially suitable for uniaxial and biaxial extensional processes to make fibers, films, foams and like products.

15 Claims, 3 Drawing Sheets sphere    200 μm

U.S. PATENT DOCUMENTS

| | | | |
|---|---|---|---|
| 1,885,256 A | | 11/1932 | Gull |
| 2,570,449 A | | 10/1951 | Horsak |
| 2,902,336 A | | 9/1959 | Hiemstra et al. |
| 3,117,014 A | | 1/1964 | Klug |
| 3,137,592 A | | 6/1964 | Protzman et al. |
| 3,280,229 A | | 10/1966 | Simons |
| 3,379,811 A | | 4/1968 | Hartmann et al. |
| 3,499,074 A | | 3/1970 | Barger et al. |
| 3,865,603 A | * | 2/1975 | Szymanski et al. ....... 106/145.1 |
| 3,954,361 A | | 5/1976 | Page |
| 4,061,611 A | * | 12/1977 | Glowaky et al. ............... 524/51 |
| 4,069,177 A | | 1/1978 | Smith |
| 4,076,663 A | | 2/1978 | Masuda et al. |
| 4,115,332 A | * | 9/1978 | Young et al. ........... 526/238.22 |
| 4,117,222 A | | 9/1978 | Holst et al. |
| 4,139,699 A | * | 2/1979 | Hernandez et al. .......... 536/109 |
| 4,243,480 A | | 1/1981 | Hernandez et al. |
| 4,340,563 A | | 7/1982 | Appel et al. |
| 4,380,570 A | | 4/1983 | Schwarz |
| 4,627,811 A | | 12/1986 | Greiser et al. |
| 4,673,438 A | | 6/1987 | Wittwer et al. |
| 4,769,081 A | * | 9/1988 | Maher ......................... 127/33 |
| 4,818,463 A | | 4/1989 | Buehning |
| 4,826,415 A | | 5/1989 | Mende |
| 4,853,168 A | | 8/1989 | Eden et al. |
| 4,855,179 A | | 8/1989 | Bourland et al. |
| 4,900,361 A | | 2/1990 | Sachetto et al. |
| 5,079,354 A | | 1/1992 | Gross et al. |
| 5,095,054 A | | 3/1992 | Lay et al. |
| 5,122,048 A | | 6/1992 | Deeds |
| 5,234,977 A | | 8/1993 | Bastioli et al. |
| 5,275,774 A | * | 1/1994 | Bahr et al. .................. 264/211 |
| 5,277,761 A | | 1/1994 | Van Phan et al. |
| 5,280,055 A | | 1/1994 | Tomka |
| 5,286,770 A | | 2/1994 | Bastioli et al. |
| 5,288,765 A | | 2/1994 | Bastioli et al. |
| 5,314,934 A | | 5/1994 | Tomka |
| 5,316,578 A | | 5/1994 | Buehler et al. |
| 5,346,936 A | | 9/1994 | Buehler et al. |
| 5,362,777 A | | 11/1994 | Tomka |
| 5,368,690 A | | 11/1994 | Solarek et al. |
| 5,382,611 A | * | 1/1995 | Stepto et al. ................... 524/47 |
| 5,405,564 A | | 4/1995 | Stepto et al. |
| 5,420,180 A | | 5/1995 | Katayama et al. |
| 5,425,987 A | | 6/1995 | Shawver et al. |
| 5,427,614 A | | 6/1995 | Wittwer et al. |
| 5,444,113 A | | 8/1995 | Sinclair et al. |
| 5,446,140 A | | 8/1995 | Maheras et al. |
| 5,454,863 A | * | 10/1995 | Foran et al. ............... 106/206.1 |
| 5,462,982 A | | 10/1995 | Bastioli et al. |
| 5,476,616 A | | 12/1995 | Schwarz |
| 5,480,923 A | | 1/1996 | Schmid et al. |
| 5,506,277 A | * | 4/1996 | Griesbach, III ............ 521/84.1 |
| 5,516,815 A | | 5/1996 | Buehler et al. |
| 5,679,145 A | | 10/1997 | Andersen et al. |
| 5,693,279 A | | 12/1997 | Feuer et al. |
| 5,703,160 A | * | 12/1997 | Dehennau et al. ........ 525/54.24 |
| 5,705,536 A | | 1/1998 | Tomka |
| 5,720,832 A | | 2/1998 | Minto et al. |
| 5,736,586 A | | 4/1998 | Bastioli et al. |
| 5,773,495 A | | 6/1998 | Haschke et al. |
| 5,844,023 A | | 12/1998 | Tomka |
| 5,866,251 A | | 2/1999 | Bastioli et al. |
| 5,874,486 A | | 2/1999 | Bastioli et al. |
| 5,945,480 A | | 8/1999 | Wang et al. |
| 6,013,223 A | | 1/2000 | Schwarz |
| 6,045,908 A | | 4/2000 | Nakajima et al. |
| 6,096,809 A | | 8/2000 | Lorcks et al. |
| 6,117,925 A | | 9/2000 | Tomka |
| 6,184,213 B1 | * | 2/2001 | Lefevre et al. ................ 514/60 |
| 6,214,907 B1 | | 4/2001 | Tomka |
| 6,218,321 B1 | | 4/2001 | Lorcks et al. |
| 6,231,970 B1 | * | 5/2001 | Andersen et al. ............ 428/332 |
| 6,235,815 B1 | | 5/2001 | Loercks et al. |
| 6,235,816 B1 | | 5/2001 | Lorcks et al. |
| 6,235,835 B1 | | 5/2001 | Niessner et al. |
| 6,238,520 B1 | | 5/2001 | Greenwood |
| 6,242,102 B1 | | 6/2001 | Tomka |
| 6,277,899 B1 | | 8/2001 | Bastioli et al. |
| 6,302,997 B1 | | 10/2001 | Hurter et al. |
| 6,303,000 B1 | | 10/2001 | Floyd et al. |
| 6,365,002 B1 | | 4/2002 | Bindzus et al. |
| 6,365,079 B1 | | 4/2002 | Winkler et al. |
| 6,372,361 B1 | | 4/2002 | Mackewicz et al. |
| 6,413,505 B1 | * | 7/2002 | Vitale et al. ............... 424/70.11 |
| 6,461,999 B1 | * | 10/2002 | Fanta et al. .................. 508/216 |
| 6,472,497 B2 | | 10/2002 | Loercks et al. |
| 6,506,824 B1 | | 1/2003 | Bastioli et al. |
| 6,517,678 B1 | | 2/2003 | Shannon et al. |
| 6,528,088 B1 | * | 3/2003 | Gilleland et al. ............ 424/451 |
| 6,709,526 B1 | * | 3/2004 | Bailey et al. .................. 127/29 |
| 2002/0015854 A1 | | 2/2002 | Billmers et al. |
| 2002/0170693 A1 | | 11/2002 | Merrette et al. |
| 2003/0022581 A1 | | 1/2003 | Tsai et al. |
| 2003/0072731 A1 | | 4/2003 | Gulian et al. |
| 2003/0099692 A1 | | 5/2003 | Lydzinski et al. |

FOREIGN PATENT DOCUMENTS

| | | |
|---|---|---|
| EP | 0 232 121 A2 | 8/1987 |
| EP | 0 080 382 B1 | 8/1988 |
| EP | 0 327 505 A | 8/1989 |
| EP | 0 522 358 A | 1/1993 |
| EP | 0 541 050 A2 | 5/1993 |
| EP | 1 035 163 A2 | 9/2000 |
| EP | 1 035 239 A2 | 9/2000 |
| EP | 1 103 655 A1 | 5/2001 |
| EP | 0 722 980 B1 | 11/2001 |
| GB | 1247474 | 9/1971 |
| JP | 61040341 | 2/1986 |
| JP | 62028410 | 2/1987 |
| JP | 4100913 | 4/1992 |
| JP | 4146217 | 5/1992 |
| JP | 6212594 | 8/1994 |
| JP | 06-269239 | 9/1994 |
| JP | 8027627 | 1/1996 |
| JP | 8260250 | 10/1996 |
| JP | 09-041224 | 2/1997 |
| JP | 9276331 | 10/1997 |
| JP | 10008364 | 1/1998 |
| SU | 375282 * | 3/1973 |
| WO | WO 98/40434 | 9/1998 |
| WO | WO 00/43423 | 7/2000 |
| WO | WO 01/38635 | 5/2001 |
| WO | WO 01/49912 A1 | 7/2001 |

OTHER PUBLICATIONS

A.J.F. de Carvalho, A.A.S. Curvelo, J.A.M. Agnelli, A First Insight on Composites of Thermoplastic Starch and Kaolin, Carbohydrate Polymers 45 (2001) 189-194, received Sep. 23, 1999; revised Jan. 26, 2000, 2001 Elsevier Science Ltd.

W. John G. McCulloch, Ph.D., The History of the Development of Melt Blowing Technology, INJ Spring 1999, pp. 66-72.

Author Unknown, A New Crop of Nonwovens, Nonwovens Industry, Feb. 2000, p. 58.

Susan Warren, Cargill, Dow Chemical to Make 'Natural Plastic', Wall Street Journal, Jan. 11, 2000.

Susanna Schlemer, Biodegradable Cellulose Fiber, Nonwovens World, Oct.-Nov. 1999, pp. 71-73.

H. Dale Wilson, Novel Polypropylene Resins for Nonwovens, Nonwovens World Oct.-Nov. 1999, p. 76.

Jan H. Schut, The New Look in Plastic—It's Paper!, Plastics Technology, Feb. 2000, pp. 52-57.

Josef L. Kokin, Lih-Shiuh Lai, Lisa L. Chedid, Effect of Starch Structure on Starch Rheological Properties, Food Technology, Jun. 1992, pp. 130-138.

Ralph D. Waniska and Marta H. Gomez, Dispersion Behavior of Starch, source unknown.

D.H. Muller, A. Krobjilowski, Meltblown Fabrics from Biodegradable Polymers, International Nonwovens Journal (Mar. 2001); abstract only.

S. Simmons et al., Thermoplastic Processing of Starch: Melt-Spinning of Starch-Based Fibers, Biodegradable Polymer Packaging (1993), Conference Proceedings, Publisher: Technomic, Lancaster, PA, pp. 171-207.

* cited by examiner

MELT PROCESSABLE STARCH COMPOSITIONS

CROSS REFERENCE TO RELATED APPLICATIONS

This application is a continuation of Ser. No. 09/914,965 filed Sep. 6, 2001, now U.S. Pat. No. 6,709,526, which is a 371 application of International Application PCT/IB00/00233 filed Mar. 7, 2000 which is a continuation-in-part application of Ser. No. 09/264,401 filed Mar. 8, 1999, abandoned.

FIELD OF INVENTION

This invention relates a novel starch composition that is substantially homogenous and has desirable rheological characteristics such that it is melt processable by conventional thermoplastic processing equipment. The present composition is particularly suitable for uniaxial and biaxial extensional processes.

BACKGROUND OF THE INVENTION

It is well recognized that starch molecules come in two forms: the substantially linear amylose polymer and the highly branched amylopectin polymer. These two forms of starch have very different properties, probably due to the ease of association of the hydroxyl groups among different molecules. The molecular structure of amylose is essentially linear with two to five relatively long branches. The average degree of polymerization of the branches is about 350 monomer units. Under conditions that provide sufficient freedom of molecular movements, primarily by dilution with suitable solvents, and in some instances, dilution coupled with heating, the linear amylose chains can be oriented into preferentially parallel alignments such that the hydroxyl groups on one chain are in close proximity with those on the adjacent chains. The alignment of neighboring amylose molecules is believed to facilitate intermolecular hydrogen bonding. Consequently the amylose molecules form strong aggregates. In contrast, the molecular structure of amylopectin is highly branched via 1,6-α linkages. The average degree of polymerization of the branches is about 25 monomer units. Due to the highly branched structure, the amylopectin molecules can not move as freely and do not align and associate as readily.

Attempts have been made to process natural starch on standard equipment and existing technology known in the plastic industry. Since natural starch generally has a granular structure, it needs to be "destructurized" and/or modified before it can be melt processed like a thermoplastic material. For destructurization, the starch is typically heated above its softening and melting temperature under a pressurized condition. Melting and disordering of the molecular structure of the starch granule takes place and a destructurized starch is obtained. Chemical or enzymatic agents may also be used to destructurize, oxidize, or derivatize the starch. Modified starches have been used to make biodegradable plastics, wherein the modified starch is blended as an additive or the minor component with petroleum-based or synthetic polymers. However, when the modified starch is processed by itself or as the major component in a blend with other materials using conventional thermoplastic processing techniques, such as molding or extrusion, the finished parts tend to have a high incidence of defects. Moreover, the modified starch (alone or as the major component of a blend) has been found to have poor melt extensibility; consequently, it cannot be successfully processed by uniaxial or biaxial extensional processes into fibers, films, foams or the like.

Previous attempts to produce starch fibers relate principally to wet-spinning processes. For Example, a starch/solvent colloidal suspension can be extruded from a spinneret into a coagulating bath. This process relies on the marked tendency of amylose to align and form strongly associated aggregates to provide strength and integrity to the final fiber. Any amylopectin present is tolerated as an impurity that adversely affects the fiber spinning process and the strength of the final product. Since it is well known that natural starch is rich in amylopectin, earlier approaches include pre-treating the natural starch to obtain the amylose-rich portion desirable for fiber spinning. Clearly this approach is not economically feasible on a commercial scale since a large portion (i.e, the amylopectin portion) of the starch is discarded. In more recent developments, natural starch, typically high in natural amylopectin content, can be wet-spun into fibers. However, the wet-spun fibers are coarse, typically having fiber diameters greater than 50 microns. Additionally, the large quantity of solvent used in this process requires an additional drying step and a recovery or treatment step of the effluent. Some references for wet-spinning starch fibers include U.S. Pat. No. 4,139,699 issued to Hernandez et al. on Feb. 13, 1979; U.S. Pat. No. 4,853,168 issued to Eden et al. on Aug. 1, 1989; and U.S. Pat. No. 4,234,480 issued to Hernandez et al. on Jan. 6, 1981.

U.S. Pat. Nos. 5,516,815 and 5,316,578 to Buehler et al. relate to starch compositions for making starch fibers from a melt spinning process. The melt starch composition is extruded through a spinnerette to produce filaments having diameters slightly enlarged relative to the diameter of the die orifices on the spinnerette (i.e., a die swell effect). The filaments are subsequently drawn down mechanically or thermo-mechanically by a drawing unit to reduce the fiber diameter. The major disadvantage of the starch composition of Buehler et al. is that it does not use high molecular weight polymers, which enhance the melt extensibility of starch compositions. Consequently, the starch composition of Buehler et al. could not be successfully melt attenuated to produce fine fibers of 25 microns or less in diameter.

Other thermoplastically processable starch compositions are disclosed in U.S. Pat. No. 4,900,361, issued on Aug. 8, 1989 to Sachetto et al.; U.S. Pat. No. 5,095,054, issued on Mar. 10, 1992 to Lay et al.; U.S. Pat. No. 5,736,586, issued on Apr. 7, 1998 to Bastioli et al.; and PCT publication WO 98/40434 filed by Hanna et al. published Mar. 14, 1997. These starch compositions do not contain the high molecular weight polymers that are necessary to achieve the desired melt viscosity and melt extensibility, which are critical material characteristics to producing fine fibers, thin films or thin-walled foams.

The art shows a need for an inexpensive and melt processable composition from natural starches. Such a melt processable starch composition should not require evaporation of a large quantity of solvents or produce a large amount of effluent during the processing operation. Moreover, such a starch composition should have melt rheological properties suitable for use in conventional plastic processing equipment The art also shows a need for a starch composition suitable for use in uniaxial or biaxial extensional processes to produce fibers, films, sheets, foams, shaped articles, and the like economically and efficiently. Specifically, the starch composition should have melt rheological properties suitable for uniaxial or biaxial extensional processes in its melt phase in a substantially continuous manner, i.e., without excessive amount of melt fracture or other defects.

SUMMARY OF THE INVENTION

The present invention relates to a starch composition that is melt processable on conventional thermoplastic equipment. Specifically, the starch composition may be successfully processed via uniaxial or biaxial extensional forces to provide a final product with good strength. Moreover the starch composition has rheological properties suitable for use in melt attenuation processes to achieve very high uniaxial or biaxial extensions, which are generally not achievable by other processes, including jet or mechanical elongation processes.

The present invention relates to a starch composition comprising starch, a polymer that is substantially compatible with starch and has a molecular weight sufficiently high to form effective entanglements or associations with neighboring starch molecules, and preferably at least one additive to improve melt flow and melt processability. Polymers having a weight-average molecular weight of at least 500,000 are particularly useful herein. The additive may be a hydroxyl plasticizer, a hydroxyl-free plasticizer, a diluent, or mixtures thereof.

The starch compositions of the present invention have the combination of melt strength and melt viscosities (shear and extensional) in the desired range such that the compositions are uniquely suitable for the melt extensional processes. The starch composition of the present invention typically has a melt shear viscosity in the range of about 0.1 to about 40 Pa·s so that the composition can be mixed, conveyed or otherwise processed on conventional processing equipment, including screw extruders, stir tanks, pumps, spinnerets, and the like. The starch composition of the present invention typically has an enhanced melt extensional viscosity due to the incorporation of the high polymers.

DETAILED DESCRIPTION OF THE INVENTION

Figure 1:
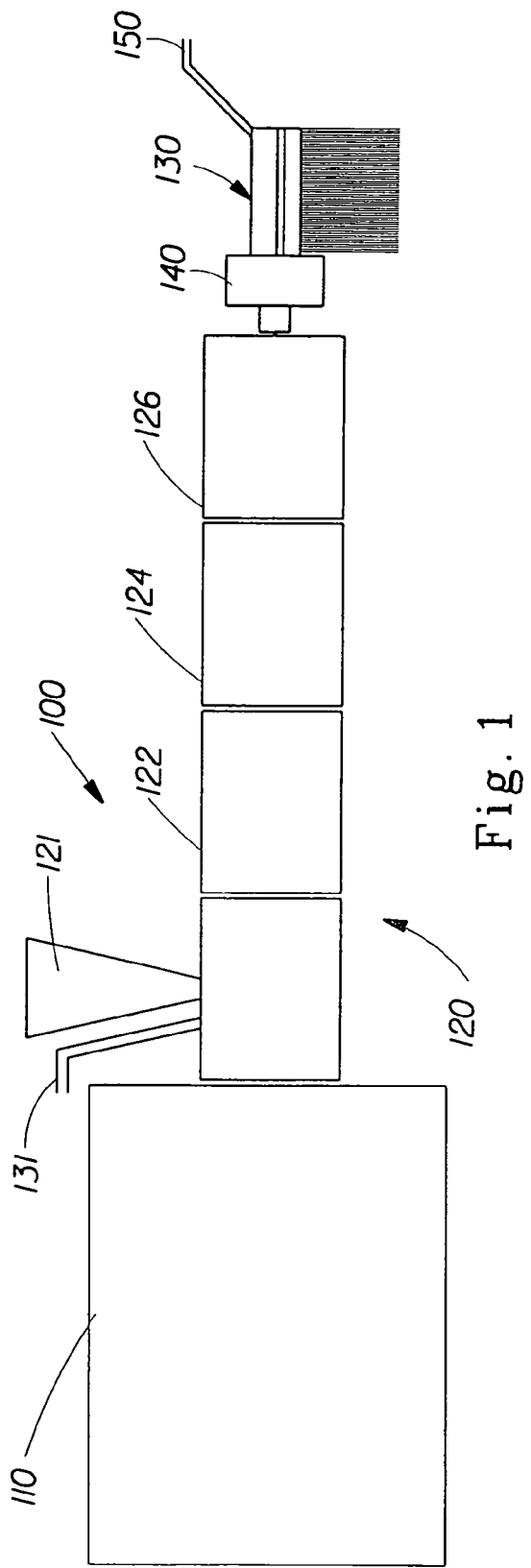
FIG. 1 shows a torque rheometer assembly having a melt blowing die used to produce fine starch fibers of the present invention.
Figure 2:
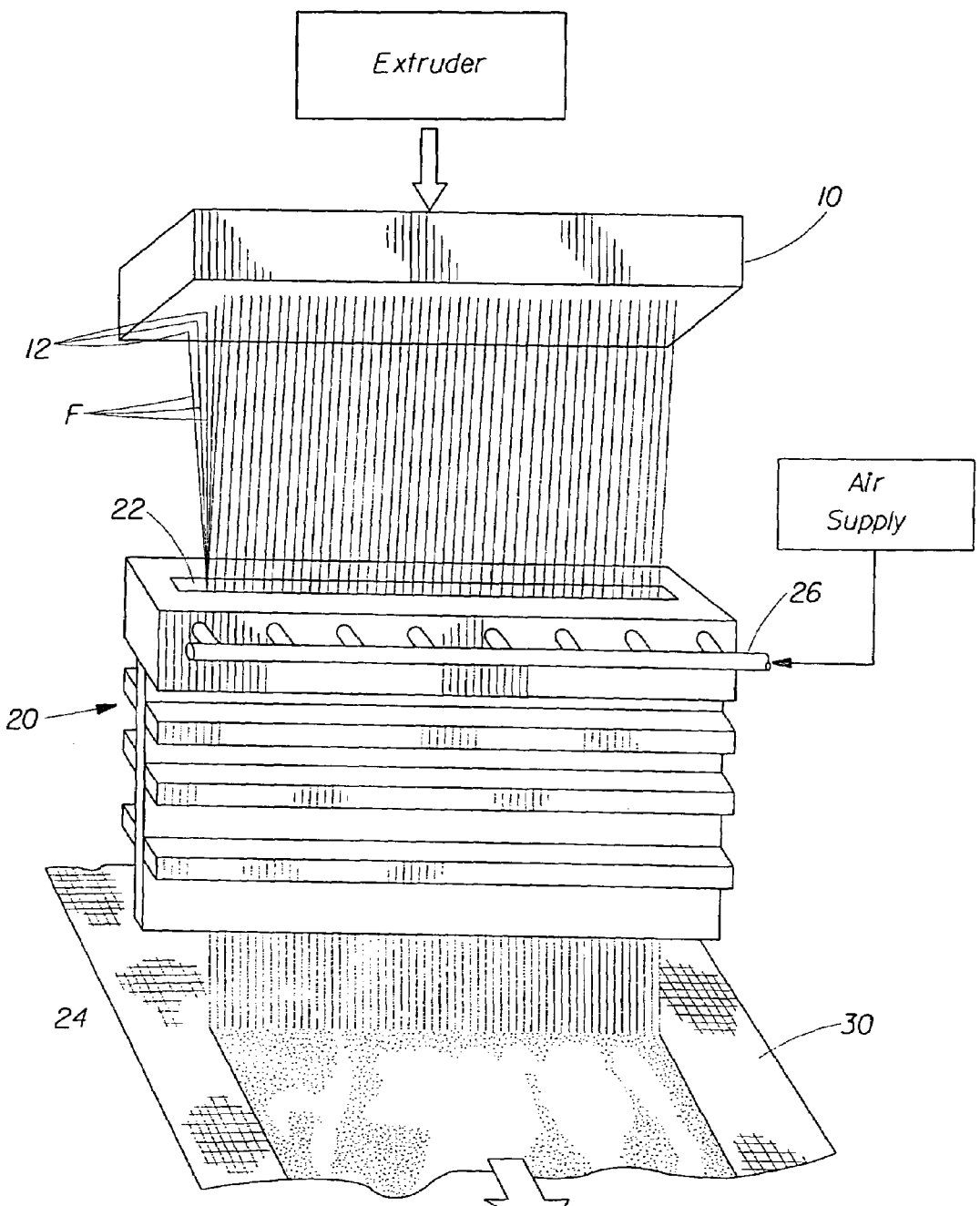
FIG. 2 shows a torque rheometer assembly used to produce starch fiber web by spun bonding.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, the term "bound water" means the water found naturally occurring in starch and before starch is mixed with other components to make the composition of the present invention. The term "free water" means the water that is added in making the composition of the present invention. A person of ordinary skill in the art would recognize that once the components are mixed in a composition, water can no longer be distinguished by its origin.

All percentages, ratios and proportions used herein are by weight percent of the composition, unless otherwise specified.

The Starch Compositions

Naturally occurring starch is generally a mixture of linear amylose and branched amylopectin polymer of D-glucose units. The amylose is a substantially linear polymer of D-glucose units joined by (1,4)-α-D links. The amylopectin is a highly branched polymer of D-glucose units joined by (1,4)-α-D links and (1,6)-α-D links at the branch points. Naturally occurring starch typically contain relatively high amylopectin, for example, corn starch (64-80% amylopectin), waxy maize (93-100% amylopectin), rice (83-84% amylopectin), potato (about 78% amylopectin), and wheat (73-83% amylopectin). Though all starches are useful herein, the present invention is most commonly practiced with high amylopectin natural starches derived from agricultural sources, which offer the advantages of being abundant in supply, easily replenishable and inexpensive.

Suitable for use herein are any naturally occurring unmodified starches and modified starches; the starch may be modified by physical, chemical, or biological processes, or combinations thereof. The choice of unmodified or modified starch for the present invention may depend on the end product desired. Also suitable for use herein are mixtures of various starches, as well as mixtures of the amylose or amylopectin fractions, having an amylopectin content in the desirable range. The starch or starch mixture useful in the present invention typically has an amylopectin content from about 20% to about 100%, preferably from about 40% to about 90%, more preferably from about 60% to about 85% by weight of the starch or mixtures thereof.

Suitable naturally occurring starches can include, but are not limited to, corn starch, potato starch, sweet potato starch, wheat starch, sago palm starch, tapioca starch, rice starch, soybean starch, arrow root starch, amioca starch, bracken starch, lotus starch, waxy maize starch, and high amylose corn starch. Naturally occurring starches particularly, corn starch and wheat starch, are the preferred starch polymers due to their economy and availability.

Physical modifications of the starch may be intramolecular or intermolecular modifications. Intramolecular modifications include reduced molecular weight and/or molecular weight distribution, changes in the polymer chain conformation, and the like. Intermolecular modifications include melting and/or disordering the starch molecules, reduction in crystallinity, crystallite size, and granular size, and the like. These physical modifications may be achieved by input of energy (such as thermal, mechanical, thermomechanical, electromagnatic, ultrasonic, and the like), pressure, moisture, fractionation, and combinations thereof.

Chemical modifications of starch typically include acid or alkali hydrolysis and oxidative chain scission to reduce molecular weight and molecular weight distribution. Suitable compounds for chemical modification of starch include organic acid such as citric acid, acetic acid, glycolic acid, and adipic acid; inorganic acids such as hydrochloric acid, sulfuric acid, nitric acid, phosphoric acid, boric acid, and partial salts of polybasic acids, e.g., $KH_2PO_4$, $NaHSO_4$; group Ia or IIa metal hydroxides such as sodium hydroxide, and potassium hydroxide; ammonia; oxidizing agents such as hydrogen peroxide, benzoyl peroxide, ammonium persulfate, potassium permagnate, sodium bicarbonate, hypochloric salts, and the like; and mixtures thereof. Preferred chemical agents of the present invention include ammonium persulfate, sulfuric acid, hydrochloric acid, and mixtures thereof.

Chemical modifications may also include derivatization of starch by reaction of its OH groups with alkylene oxides, and other ether-, ester-, urethane-, carbamate-, or isocyanate-forming substances. Hydroxylalkyl, acetyl, or carbamate starches or mixtures thereof are preferred chemically modified starches. The degree of substitution of the chemically modified starch is 0.05 to 3.0, preferably 0.05 to 0.2.

Biological modifications of starch include bacterial digestion of the carbohydrate bonds, or enzymatic hydrolysis using enzymes such as amylase, amylopectase, and the like.

The starch typically has a bound water content of about 5% to 16% by weight of starch. A water content of about 8% to about 12% by weight of starch is particularly preferred. The amylose content of the starch is typically from 0% to about 80%, preferably from about 20% to about 35%, by weight of starch.

Natural, unmodified starch generally has a very high average molecular weight and a broad molecular weight distribution (e.g. natural corn starch has an average molecular weight of about 10,000,000 and a molecular weight distribution greater than 1000). The average molecular weight of starch can be reduced to the desirable range for the present invention by chain scission (oxidative or enzymatic), hydrolysis (acid or alkaline catalyzed), physical/mechanical degradation (e.g., via the thermomechanical energy input of the processing equipment), or combinations thereof. These reactions also reduce the molecular weight distribution of starch to less than about 600, preferably to less than about 300. The thermomechanical method and the oxidation method offer an additional advantage in that they are capable of being carried out in situ of the melt spinning process.

In one embodiment, the natural starch is hydrolyzed in the presence of acid, such as hydrochloric acid or sulfuric acid, to reduce the molecular weight and molecular weight distribution. In another embodiment, a chain scission agent may be incorporated into the melt spinnable starch composition such that the chain scission reaction takes place substantially concurrently with the blending of the starch with other components. Nonlimiting examples of oxidative chain scission agents suitable for use herein include ammonium persulfate, hydrogen peroxide, hypochlorate salts, potassium permanganate, and mixtures thereof. Typically, the chain scission agent is added in an amount effective to reduce the weight-average molecular weight of the starch to the desirable range. For example, it is found that for uniaxial or biaxial melt attenuation processes, the starch should have a weight-average molecular weight ranging from about 1,000 to about 2,000,000, preferably from about 1,500 to about 800,000, more preferably from about 2,000 to about 500,000. It is found that compositions having modified starch in the above molecular weight range have a suitable melt shear viscosity, and thus improved melt processability. The improved melt processability is evident in less interruptions of the process (e.g., reduced breakage, shots, defects, hang-ups) and better surface appearance and strength properties of the product.

Typically the composition herein comprises from about 20 to about 99.99 wt %, preferably from about 30 to about 95 wt %, and more preferably from about 50 to about 85 wt %, of unmodified and/or modified starch. The weight of starch in the composition includes starch and its naturally occurring bound water content. It is known that additional free water may be incorporated as the polar solvent or plasticizer, and not included in the weight of the starch.

High molecular weight polymers (hereinafter "high polymers") which are substantially compatible with starch are also useful herein. The molecular weight of a suitable polymer should be sufficiently high to effectuate entanglements and/or associations with starch molecules. The high polymer preferably has a substantially linear chain structure, though a linear chain having short (C1-C3) branches or a branched chain having one to three long branches are also suitable for use herein. As used herein, the term "substantially compatible" means when heated to a temperature above the softening and/or the melting temperature of the composition, the high polymer is capable of forming a substantially homogeneous mixture with the starch (i.e., the composition appears transparent or translucent to the naked eye).

The Hildebrand solubility parameter ($\delta$) can be used to estimate the compatibility between starch and the polymer. Generally, substantial compatibility between two materials can be expected when their solubility parameters are similar. It is known that water has a $\delta_{water}$ value of 48.0 MPa$^{1/2}$, which is the highest among common solvents, probably due to the strong hydrogen bonding capacity of water. Starch typically has a $\delta_{starch}$ value similar to that of cellulose (about 34 MPa$^{1/2}$).

Without being bound by theory, it is believed that polymers suitable for use herein preferably interact with the starch molecules on the molecular level in order to form a substantially compatible mixture. The interactions range from the strong, chemical type interactions such as hydrogen bonding between polymer and starch, to merely physical entanglements between them. The polymers useful herein are preferably high molecular weight, substantially linear chain molecules. The highly branched structure of a amylopectin molecule favors the branches to interact intramolecularly, due to the proximity of the branches within a single molecule. Thus, it is believed that the amylopectin molecule has poor or ineffective entanglements/interactions with other starch molecules, particularly other amylopectin molecules. The compatibility with starch enables suitable polymers to be intimately mixed and chemically interact and/or physically entangle with the branched amylopectin molecules such that the amylopectin molecules associate with one another via the polymers. The high molecular weight of the polymer enables it to simultaneously interact/entangle with several starch molecules. That is, the high polymers function as molecular links for starch molecules. The linking function of the high polymers is particularly important for starches high in amylopectin content. The entanglements and/or associations between starch and polymers enhance the melt extensibility of the starch composition such that the composition is suitable for extensional processes. In one embodiment, it is found that the composition can be melt attenuated uniaxially to a very high draw ratio (greater than 1000).

In order to effectively form entanglements and/or associations with the starch molecules, the high polymer suitable for use herein should have a weight-average molecular weight of at least 500,000. Typically the weight average molecular weight of the polymer ranges from about 500,000 to about 25,000,000, preferably from about 800,000 to about 22,000,000, more preferably from about 1,000,000 to about 20,000,000, and most preferably from about 2,000,000 to about 15,000,000. The high molecular weight polymers are preferred due to the ability to simultaneously interact with several starch molecules, thereby increasing extensional melt viscosity and reducing melt fracture.

Suitable high polymers have a $\delta_{Polymer}$ such that the difference between $\delta_{starch}$ and $\delta_{polymer}$ is less than about 10 MPa$^{1/2}$, preferably less than about 5 MPa$^{1/2}$, and more preferably less than about 3 MPa$^{1/2}$. Nonlimiting examples of suitable high polymers include polyacrylamide and derivatives such as carboxyl modified polyacrylamide; acrylic polymers and copolymers including polyacrylic acid, polymethacrylic acid, and their partial esters; vinyl polymers including polyvinyl alcohol, polyvinylacetate, polyvinylpyrrolidone, polyethylene vinyl acetate, polyethyleneimine, and the like; polyamides; polyalkylene oxides such as polyethylene oxide, polypropylene oxide, polyethylenepropylene oxide, and mixtures thereof. Copolymers made from mixtures of monomers selected from any of the aforementioned polymers are also suitable herein. Other exemplary high polymers include water soluble polysaccharides such as alginates, carrageenans, pectin and derivatives, chitin and derivatives, and the like; gums such as guar gum, xanthum gum, agar, gum arabic, karaya gum, tragacanth gum, locust bean gum, and like gums; water soluble derivatives of cellulose, such as alkylcellulose, hydroxyalkylcellulose, carboxyalkylcellulose, and the like; and mixtures thereof.

Some polymers (e.g., polyacrylic acid, polymethacrylic acid) are generally not available in the high molecular weight range (i.e., 500,000 or higher). A small amount of crosslinking agents may be added to create branched polymers of suitably high molecular weight useful herein.

The high polymer is added to the composition of the present invention in an amount effective to visibly reduce the melt fracture and capillary breakage of fibers during the spinning process such that substantially continuous fibers having relatively consistent diameter can be melt spun. These polymers are typically present in the range from about 0.001 to about 10 wt %, preferably from about 0.005 to about 5 wt %, more preferably from about 0.01 to about 1 wt %, and most preferably from about 0.05 to about 0.5 wt % of the composition. It is surprising to find that at a relatively low concentration, these polymers significantly improve the melt extensibility of the starch composition.

The starch compositions may optionally include additives to enhance melt flow and melt processability, particularly the extensibility of the composition under the melt processing conditions. The additives may function as plasticizers and/or diluents to reduce the melt shear viscosity of the starch composition. The plasticizers are added to the composition of the present invention in an amount effective to improve the flow, hence, the melt processability. The plasticizers may also improve the flexibility of the final products, which is believed to be due to the lowering of the glass transition temperature of the composition by the plasticizer. The plasticizers should preferably be substantially compatible with the polymeric components of the present invention so that the plasticizers may effectively modify the properties of the composition. As used herein, the term "substantially compatible" means when heated to a temperature above the softening and/or the melting temperature of the composition, the plasticizer is capable of forming a substantially homogeneous mixture with starch (i.e., the composition appears transparent or translucent to the naked eye).

Suitable for use herein as hydroxyl plasticizers are organic compounds having at least one hydroxyl group, preferably a polyol. Without being bound by theory, it is believed that the hydroxyl groups of the plasticizers enhance compatibility by forming hydrogen bonds with the starch matrix material. Nonlimiting examples of useful hydroxyl plasticizers include sugars such as glucose, sucrose, fructose, raffinose, maltodextrose, galactose, xylose, maltose, lactose, mannose, erythrose, glycerol, and pentaerythritol; sugar alcohols such as erythritol, xylitol, maltitol, mannitol and sorbitol; polyols such as ethylene glycol, propylene glycol, dipropylene glycol, butylene glycol, hexane triol, and the like, and polymers thereof; and mixtures thereof.

Also useful herein as hydroxyl plasticizers are poloxomers (polyoxyethylene/polyoxypropylene block copolymers) and poloxamines (polyoxyethylene/polyoxypropylene block copolymers of ethylene diamine). Suitable "poloxomers" comprise block copolymers of polyoxyethylene/polyoxypropylene having the following structure:

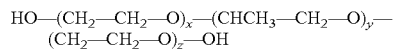

wherein x has a value ranging from about 2 to about 40, y has a value ranging from about 10 to about 50, and z has a value ranging from about 2 to about 40, and preferably x and z have the same value. These copolymers are available as Pluronic® from BASF Corp., Parsippany, N.J. Suitable poloxamers and poloxamines are available as Synperonic® from ICI Chemicals, Wilmington, Del., or as Tetronic® from BASF Corp., Parsippany, N.J.

Also suitable for use herein as hydroxyl-free plasticizers are other hydrogen bond forming organic compounds which do not have hydroxyl group, including urea and urea derivatives; anhydrides of sugar alcohols such as sorbitan; animal proteins such as gelatin; vegetable proteins such as sunflower protein, soybean protein, and cotton seed protein; and mixtures thereof. All of the plasticizers may be used alone or in mixtures thereof.

Typically, the hydroxyl plasticizer comprises from about 1 wt % to about 70 wt %, more preferably from about 2 wt % to about 60 wt %, most preferably from about 3 wt % to about 40 wt % of the starch composition. The hydroxyl-free plasticizer typically comprises from about 0.1 wt % to about 70 wt %, preferably from about 2 wt % to about 50 wt %, more preferably from about 3 wt % to about 40 wt % of the starch composition.

In one embodiment, a mixture of the hydroxyl and hydroxyl-free plasticizers is used, wherein the hydroxyl plasticizers are sugars, such as sucrose, fructose, and sorbitol, and the hydroxyl-free plasticizers are urea and urea derivatives. It is found that urea and its derivatives in the starch composition of the present invention have a strong tendency to crystallize, that is, crystallization of urea and its derivatives occurs even under fast cooling condition such as melt blowing, spun bonding, melt extrusion, wet spinning, and the like. Therefore, urea and urea derivatives may be used as solidifying agents for modifying or controlling the solidification rate of the starch composition of the present invention. In a preferred embodiment, a mixture of sucrose and urea is added to the starch/polymer composition in an amount effective to achieve the desired melt processability and solidification rate.

Diluents such as polar solvents may be added to the starch compositions of the present invention to adjust the melt shear viscosity and enhance the melt spinnability of the starch compositions. Generally, the melt shear viscosity decreases in a nonlinear manner as the diluent content is increased. Typically, the diluent is added in an amount from about 5 wt % to about 60 wt %, preferably from about 7 wt % to about 50 wt %, more preferably from about 10 wt % to about 30 wt %, of the total composition.

Suitable for use herein as diluents are polar solvents having a solubility parameter δ ranging from about 19 to about 48 $MPa^{1/2}$, preferably from about 24 to about 48 $MPa^{1/2}$, and more preferably from about 28 to about 48 $MPa^{1/2}$. Nonlimiting examples include water, C1-C18 linear or branched alcohols, DMSO (dimethyl sulphoxide), formamide and derivatives such as N-methyl formamide, N-ethyl formamide, acetamide and derivatives such as methyl acetamide, Cellosolv® (a glycol alkyl ether) and derivatives, such as butyl Cellosolv®, benzyl Cellosolv®, Cellosolv® acetate (all Cellosolv® and derivatives are available from J.T. Baker, Phillipsburg, N.J.), hydrazine, and ammonia. It is also known that the δ value of a solvent mixture can be determined by volume-averaging the δ values of the individual solvents. Therefore, mixed solvents having δ values within the above-identified range (i.e., from about 19 to about 48 $MPa^{1/2}$) are also suitable for use herein. For example, a mixed solvent of DMSO/water having a composition of 90/10 v/v would have a δ value of about 31.5; such a mixed solvent system is suitable for use herein.

It is found that polar solvents capable of forming hydrogen bonding are more effective in lowering the melt viscosity of the composition. As such, a lower amount of the polar solvent is sufficient to adjust the viscosity to the desired range for melt spinning. Using a lower amount of the polar solvent provides a further advantage of reducing the need for an evaporation step during or subsequent to the melt processing step, which results in operating cost advantages such as lower energy consumption and lower solvent recovery costs, as well as lower costs for environmental/regulatory compliance.

The starch composition may optionally include liquid or volatile processing aids which function mainly as viscosity modifiers of the melt compositions. The processing aid is substantially volatized and removed during the melt processing stage such that only a residual/trace amount remains in the final product. Thus, they do not adversely affect the strength, modulus or other properties of the final product. The polar solvents disclosed above may also function as volatile processing aids. Other nonlimiting examples include carbonates such as sodium bicarbonate.

Optionally, other ingredients may be incorporated into the spinnable starch composition to modify the processability and/or to modify physical properties such as elasticity, tensile strength and modulus of the final product. Nonlimiting examples include oxidation agents, cross-linking agents, emulsifiers, surfactants, debonding agents, lubricants, other processing aids, optical brighteners, antioxidants, flame retardants, dyes, pigments, fillers, proteins and their alkali salts, biodegradable synthetic polymers, waxes, low melting synthetic thermoplastic polymers, tackifying resins, extenders, wet strength resins and mixtures thereof. These optional ingredients may be present in quantities ranging from about 0.1% to about 70%, preferably from about 1% to about 60%, more preferably from about 5% to about 50%, and most preferably from about 10% to about 50%, by weight of the composition.

Exemplary biodegradable synthetic polymers include polycaprolactone; polyhydroxyalkanoates including polyhydroxybutyrates, and polyhydroxyvalerates; polylactides; and mixtures thereof.

Lubricant compounds may further be added to improve the flow properties of the starch material during the processes used for producing the present invention. The lubricant compounds can include animal or vegetable fats, preferably in their hydrogenated form, especially those which are solid at room temperature. Additional lubricant materials include mono-glycerides and di-glycerides and phosphatides, especially lecithin. For the present invention, a preferred lubricant compound includes the mono-glyceride, glycerol monostearate.

Further additives including inorganic particles such as the oxides of magnesium, aluminum, silicon, and titanium may be added as inexpensive fillers or extenders. Additionally, additives such as inorganic salts, including alkali metal salts, alkaline earth metal salts, phosphate salts, etc., may be used.

Other additives may be desirable depending upon the particular end use of the product contemplated. For example, in products such as toilet tissue, disposable towels, facial tissues and other similar products, wet strength is a desirable attribute. Thus, it is often desirable to add to the starch polymer cross-linking agents known in the art as "wet strength" resins.

A general dissertation on the types of wet strength resins utilized in the paper art can be found in TAPPI monograph series No. 29, Wet Strength in Paper and Paperboard, Technical Association of the Pulp and Paper Industry (New York, 1965). The most useful wet strength resins have generally been cationic in character. Polyamide-epichlorohydrin resins are cationic polyamide amine-epichlorohydrin wet strength resins which have been found to be of particular utility. Suitable types of such resins are described in U.S. Pat. No. 3,700,623, issued on Oct. 24, 1972, and U.S. Pat. No. 3,772,076, issued on Nov. 13, 1973, both issued to Keim and both being hereby incorporated by reference. One commercial source of a useful polyamide-epichlorohydrin resin is Hercules, Inc. of Wilmington, Del., which markets such resins under the mark Kymene®.

Glyoxylated polyacrylamide resins have also been found to be of utility as wet strength resins. These resins are described in U.S. Pat. No. 3,556,932, issued on Jan. 19, 1971, to Coscia, et al. and U.S. Pat. No. 3,556,933, issued on Jan. 19, 1971, to Williams et al., both patents being incorporated herein by reference. One commercial source of glyoxylated polyacrylamide resins is Cytec Co. of Stanford, Conn. which markets one such resin under the mark Parez® 631NC.

It is found that when suitable cross-linking agent such as Parez® 631NC is added to the starch composition of the present invention under acidic condition. The composition is rendered water insoluble. That is, the water solubility of the composition, as tested by the Test Method described hereinafter, is less than 30%, preferably less than 20%, more preferably less than 10% and most preferably less than 5%. The products such as fibers and films made from such a composition are also water insoluble.

Still other water-soluble cationic resins finding utility in this invention are urea formaldehyde and melamine formaldehyde resins. The more common functional groups of these polyfunctional resins are nitrogen containing groups such as amino groups and methylol groups attached to nitrogen. Polyethylenimine type resins may also find utility in the present invention. In addition, temporary wet strength resins such as Caldas® 10 (manufactured by Japan Carlit) and CoBond® 1000 (manufactured by National Starch and Chemical Company) may be used in the present invention.

For the present invention, a suitable cross-linking agent is added to the composition in quantities ranging from about 0.1% by weight to about 10% by weight, more preferably from about 0.1% by weight to about 3% by weight.

The Rheology of the Starch Compositions

The rheological behavior of the starch composition is an important consideration for selecting suitable materials and fabrication equipment/processes. Many factors contribute to the rheological behavior of the starch composition, including the amount and the type of polymeric components used, the molecular weight and molecular weight distribution of the components, the amount and type of additives (e.g., plasticizers, processing aids), the processing conditions such as temperature, pressure, rate of deformation, and relative humidity, and in the case of non-Newtonian materials, the deformation history (i.e., a time or strain history dependence).

The starch composition of the present invention typically has a high solid content (i.e., a concentration above a critical concentration $C^*$) such that a dynamic or fluctuating entangled network is formed wherein the starch molecules and the high polymers become associated and disassociated temporally. The association may be in the form of physical entanglements, van der Waals forces, or chemical interactions such as hydrogen bonding. The starch composition having the entangled network structure exhibits melt flow behavior typical of a non-Newtonian fluid.

The starch composition of the present invention may exhibit a strain hardening behavior, that is, the extensional viscosity increases as the strain or deformation increases. Typically, a Newtonian fluid exhibit a linear relationship between stress/force and strain. That is, there is no strain hardening behavior in a Newtonian fluid. On the other hand, a non-Newtonian fluid may exhibiting an increase in force at higher strain (i.e, strain hardening) while still exhibit a linear force-strain relationship at lower strain (i.e, Newtonian-like).

The strain experienced by a fluid element in a non-Newtonian fluid is dependent on its kinematic history, that is $$\varepsilon = \int_0^t \varepsilon \cdot (t') \partial t'$$

This time or history dependent strain is called the Hencky strain ($\epsilon_H$). For an ideal homogeneous uniaxial elongation, the strain rate experienced by every fluid element is equal to the strain imposed by the applied stress, such as the stresses applied externally by the instrument, device or process. In such an ideal case, the Hencky strain correlates directly with the sample deformation/elongation $$\epsilon_H = ln(L/L_O)$$

Such an ideal strain response to applied stress is most often observed in Newtonian fluids.

The Trouton ratio (Tr) is often used to express the extensional flow behavior. The Trouton ratio is defined as the ratio between the extensional viscosity ($\eta_e$) and the shear viscosity ($\eta_s$), $$Tr = \eta_e(\epsilon^*, t)/\eta_s$$

wherein the extensional viscosity $\eta_e$ is dependent on the deformation rate ($\epsilon^*$) and time (t). For a Newtonian fluid, the uniaxial extension Trouton ratio has a constant value of 3. For a non-Newtonian fluid, the extensional viscosity is dependent on the deformation rate ($\epsilon^*$) and time (t).

Shear viscosity ($\eta_s$) relates to the melt processability of the starch composition using standard polymer processing techniques, such as extrusion, blow molding, compression molding, injection molding and the like. A starch composition having a shear viscosity, measured according to the Test Method disclosed hereinafter, of less than about 30 Pa·s, preferably from about 0.1 to about 10 Pa·s, more preferably from about 1 to about 8 Pa·s, is useful in the melt attenuation processes herein. Some starch compositions herein may have low melt viscosity such that they may be mixed, conveyed, or otherwise processed in traditional polymer processing equipment typically used for viscous fluids, such as a stationary mixer equipped with metering pump and spinneret. The shear viscosity of the starch composition may be effectively modified by the molecular weight and molecular weight distribution of the starch, the molecular weight of the high polymer, and the amount of plasticizers and/or solvents used. It is found that reducing the average molecular weight of the starch is an effective way to lower the shear viscosity of the composition.

It is generally known that melt shear viscosity is a material property useful for evaluating melt processability of the material in traditional thermoplastic processes such as injection molding or extrusion. For conventional fiber spinning thermoplastics such as polyolefins, polyamides and polyesters, there is a strong correlation between shear viscosity and extensional viscosity of these conventional thermoplastic materials and blends thereof. That is, the spinnability of the material can be determined simply by the melt shear viscosity, even though the spinnablity is a property controlled primarily by melt extensional viscosity. The correlation is quite robust such that the fiber industry has relied on the melt shear viscosity in selecting and formulating melt spinnable materials. The melt extensional viscosity has rarely been used as an industrial screening tool.

It is therefore surprising to find that the starch compositions of the present invention do not exhibit such a correlation between shear and extensional viscosities. Specifically, when a high polymer selected according to the present invention is added to a starch composition, the shear viscosity of the composition remains relatively unchanged, or even decreases slightly. Based on conventional wisdom, such a starch composition would exhibit decreased melt processability and would not be suitable for melt extensional processes. However, it is surprisingly found that the starch composition herein shows a significant increase in extensional viscosity when even a small amount of high polymer is added. Consequently, the starch composition herein is found to have enhanced melt extensibility and is suitable for melt extensional processes (e.g., blow molding, spun bonding, blown film molding, foam molding, and the like).

Extensional or elongational viscosity ($\eta_e$) relates to melt extensibility of the composition, and is particularly important for extensional processes such as fiber, film or foam making. The extensional viscosity includes three types of deformation: uniaxial or simple extensional viscosity, biaxial extensional viscosity, and pure shear extensional viscosity. The uniaxial extensional viscosity is important for uniaxial extensional processes such as fiber spinning, melt blowing, and spun bonding. The other two extensional viscosities are important for the biaxial extension or forming processes for making films, foams, sheets or parts. It is found that the properties of the high polymers have a significant effect on melt extensional viscosity. The high polymers useful for enhancing the melt extensibility of the starch composition of the present invention are typically high molecular weight, substantially linear polymers. Moreover, high polymers that are substantially compatible with starch are most effective in enhancing the melt extensibility of the starch composition.

It has been found that starch compositions useful for melt extensional processes typically hasve their extensional viscosity increased by a factor of at least 10 when a selected high polymer is added to the composition. Typically, the starch compositions of present invention show an increase in the extensional viscosity of about 10 to about 500, preferably of about 20 to about 300, more preferably from about 30 to about 100, when a selected high polymer is added.

It has also been found that melt processable compositions of the present invention typically have a Trouton ratio of at least about 3. Typically, the Trouton ratio ranges from about 10 to about 5,000, preferably from about 20 to about 1,000, more preferably from about 30 to about 500, when measured at 90° C. and 700 s$^{-1}$.

When the starch composition of the present composition is subjected to an uniaxial extensional process, a draw ratio, expressed in ($D_O^2/D^2$) wherein $D_O$ is the diameter of filament before drawing and D is the diameter of the drawn fiber, greater than 1000 can be easily achieved. The starch composition of the present invention typically achieves a draw ratio from about 5 to about 6,000, preferably from about 10 to about 3,000, more preferably from about 20 to about 1,000 and most preferably from about 30 to about 500. More specifically, the starch composition of the present invention has sufficient melt extensibility to be melt drawn to fine fibers having a finite average diameter of less than 50 microns, preferably less than 25 microns, more preferably less than 15 microns, even more preferably less than 10 microns, and most preferably less than 5 microns.

When the starch composition of the present invention is subjected to a biaxial extensional process, the enhanced melt extensibility of the composition allows it to be melt drawn to films having a finite average caliper of less than 0.8 mils, preferably less than 0.6 mils, more preferably less than 0.4 mils, even more preferably less than 0.2 mils, and most preferably less than 0.1 mils.

The starch composition herein is processed in a flowable state, which typically occurs at a temperature at least equal to or higher than its melting temperature. Therefore, the processing temperature range is controlled by the melting temperature of the starch composition, which is measured according to the Test Method described in detail herein. The melting temperature of the starch composition herein ranges from about 80 to 180° C., preferably from about 85 to about 160° C., and more preferably from about 90 to about 140° C. It is to be understood that some starch compositions may not exhibit pure "melting" behavior. As used herein, the term "melting temperature" means the temperature or the range of temperature at or above which the composition melts or softens.

Exemplary uniaxial extensional processes suitable for the starch compositions include melt spinning, melt blowing, and spun bonding. These processes are described in detail in U.S. Pat. No. 4,064,605, issued on Dec. 27, 1977 to Akiyama et al.; U.S. Pat. No. 4,418,026, issued on Nov. 29, 1983 to Blackie et al.; U.S. Pat. No. 4,855,179, issued on Aug. 8, 1989 to Bourland et al.; U.S. Pat. No. 4,909,976, issued on Mar. 20, 1990 to Cuculo et al.; U.S. Pat. No. 5,145,631, issued on Sep. 8, 1992 to Jezic; U.S. Pat. No. 5,516,815, issued on May 14, 1996 to Buehler et al.; and U.S. Pat. No. 5,342,335, issued on Aug. 30, 1994 to Rhim et al.; the disclosure of all of the above are incorporated herein by reference. The resultant products may find use in filters for air, oil and water; vacuum cleaner filters; furnace filters; face masks; coffee filters, tea or coffee bags; thermal insulation materials and sound insulation materials; nonwovens for one-time use sanitary products such as diapers, feminine pads, and incontinence articles; biodegradable textile fabrics for improved moisture absorption and softness of wear such as microfiber or breathable fabrics; an electrostatically charged, structured web for collecting and removing dust; reinforcements and webs for hard grades of paper, such as wrapping paper, writing paper, newsprint, corrugated paper board, and webs for tissue grades of paper such as toilet paper, paper towel, napkins and facial tissue; medical uses such as surgical drapes, wound dressing, bandages, dermal patches and self-dissolving sutures; and dental uses such as dental floss and toothbrush bristles. The fibrous web may also include odor absorbants, termite repellants, insecticides, rodenticides, and the like, for specific uses. The resultant product absorbs water and oil and may find use in oil or water spill clean-up, or controlled water retention and release for agricultural or horticultural applications. The resultant starch fibers or fiber webs may also be incorporated into other materials such as saw dust, wood pulp, plastics, and concrete, to form composite materials, which can be used as building materials such as walls, support beams, pressed boards, dry walls and backings, and ceiling tiles; other medical uses such as casts, splints, and tongue depressors; and in fireplace logs for decorative and/or burning purpose.

The melt rheological behavior of the present starch composition also makes it suitable for use in conventional thermoplastic processes that involves biaxial extension of the material. By having the proper melt shear viscosity and biaxial extensional viscosity, the starch compositions of the present invention may substantially reduce the occurrence of tearing, surface defects, and other breakdowns or defects that interrupt continuous processes and produce unsatisfactory products. These processes include blow molding, blown film extrusion or coextrusion, vacuum forming, pressure forming, compression molding, transfer molding and injection molding. Nonlimiting examples of these processes are described in details in U.S. Pat. No. 5,405,564, issued on Apr. 11, 1995 to Stepto et al.; U.S. Pat. No. 5,468,444, issued on Nov. 21, 1995 to Yazaki et al.; U.S. Pat. No. 5,462,982, issued on Oct. 31, 1995 to Bastioli et al.; the disclosure of all of the above are hereby incorporated by reference. The articles produced by these processes include sheets, films, coatings, laminates, pipes, rods, bags, and shaped articles (such as bottles, containers). The articles may find use as bags such as shopping bags, grocery bags, and garbage bags; pouches for food storage or cooking; microwavable containers for frozen food; and pharmaceutical uses such as capsules or coatings for medicine. The films may be substantially transparent for use as food wraps, shrink wraps or windowed envelopes. The films may also be further processed for use as an inexpensive, biodegradable carrier for other materials such as seeds or fertilizers. Adhesives may be applied to the films or sheets for other uses such as labels.

The starch compositions of the present invention may also be made into a foamed structure by controlled removal of the volatile components (e.g., water, polar solvents). However, foaming or expanding agents are generally incorporated to produce articles having foamed or porous internal structure. Exemplary foaming or expanding agents include carbon dioxide, n-pentane, and carbonate salts such as sodium bicarbonate, either alone or in combination with a polymeric acid which has lateral carboxyl groups (e.g., polyacrylic acid, ethylene-acrylic copolymer). Nonlimiting examples of the foaming and forming processes are described in U.S. Pat. No. 5,288,765, issued on Feb. 22, 1994 to Bastioli et al.; U.S. Pat. No. 5,496,895, issued on Mar. 5, 1996 to Chinnaswamy et al.; U.S. Pat. No. 5,705,536, issued on Jan. 6, 1998 to Tomka; and U.S. Pat. No. 5,736,586, issued on Apr. 7, 1998 to Bastioli et al.; the disclosures of which are hereby incorporated by reference. The resultant products may find use in egg cartons; foamed cups for hot beverages; containers for fast food; meat trays; plates and bowls for one-time use such as at picnic or parties; packaging materials, either loose-fill or molded to conform to the packed article (e.g., a computer shipping package); thermal insulation materials; and noise insulation or sound proofing materials.

Test Methods

A. Shear Viscosity

The shear viscosity of the composition is measured using a rotational viscometer (Model DSR 500, manufactured by Rheometrics). A preheated sample composition is loaded into the barrel section of the rheometer, and substantially fills the barrel section (about 60 grams of sample is used). The barrel is held at a test temperature of 90° C. After the loading, air generally bubbles to the surface and does create problems for the run. For a more viscous samples, compaction prior to running the test may be used to rid the molten sample of entrapped air. The viscometer is programmed to ramp the applied stress from 10 dyne/cm to 5000 dyne/cm. The strain experienced by the sample is measure by a strain gauge. The apparent viscosity of the composition can be derived therefrom. Then log (apparent shear viscosity) is plotted against log (shear rate) and the plot is fitted by the power law $\eta = K \gamma^{n-1}$, wherein K is a material constant, $\gamma$ is the shear rate. The reported shear viscosity of the starch composition herein is an extrapolation to a shear rate of 700 s$^{-1}$ using the power law relation.

B. Extensional Viscosity

The extensional viscosity is measured using a capillary rheometer (Model Rheograph 2003, manufactured by Geottfert). The measurements are conducted using an orifice die having a diameter D of 0.5 mm and a length L of 0.25 mm (i.e., L/D=0.5). The die is attached to the lower end of a barrel, which is held at a test temperature of 90° C. A preheated sample composition is loaded into the barrel section of the rheometer, and substantially fills the barrel section. After the loading, air generally bubbles to the surface and does create problems for the run. For more viscous compositions, compaction prior to running the test may be used to rid the molten sample of entrapped air. A piston is programmed to push the sample from the barrel through the orifice die at a chosen rate. As the sample goes from the barrel through the orifice die, the sample experiences a pressure drop. An apparent viscosity can be obtained from the pressure drop and the flow rate of the sample through the orifice die. Corrections are often applied to the apparent viscosity following procedures generally known in the art. A shear correction factor and Cogswell equation are applied to the calculation of the extensional viscosity. The corrected extensional viscosity at 700 s$^{-1}$ is reported.

It is known that the extensional viscosity can be measured using an orifice die and applying the correction factors, following the method described herein. More details of extensional viscosity measurements are disclosed in S. H. Spielberg et al., *The Role Of End-Effects On Measurements Of Extensional Viscoistv In Filament Stretching Rheometers*, Journal of Non-Newtonian Fluid Mechanics, Vol. 64, 1996, p. 229-267; Bhattacharya, et al., *Uniaxial Extensional Viscoisty During Extrusion Cooking From Entrance Pressure Drop Method*, Journal of Food Science, Vol. 59, No. 1, 1994, p. 221-226; both are hereby incorporated by reference. It is also known that the extensional viscosity can be measured using a hyperbolic or semi-hyperbolic die. Detailed disclosure of extensional viscosity measurements using a semi-hyperbolic die is disclosed in U.S. Pat. No. 5,357,784, issued Oct. 25, 1994 to Collier, the disclosure of which is incorporated herein by reference.

C. Molecular Weight and Molecular Weight Distribution

The weight-average molecular weight (Mw) and molecular weight distribution (MWD) of starch are determined by Gel Permeation Chromatography (GPC) using a mixed bed column. Parts of the instrument are as follows:

| | |
|---|---|
| Pump | Waters Model 600E |
| System controller | Waters Model 600E |
| Autosampler | Waters Model 717 Plus |
| Column | PL gel 20 μm Mixed A column (gel molecular weight ranges from 1,000 to 40,000,000) having a length of 600 mm and an internal diameter of 7.5 mm. |
| Detector | Waters Model 410 Differential Refractometer |
| GPC software | Waters Millenium ® software |

The column is calibrated with Dextran standards having molecular weights of 245,000; 350,000; 480,000; 805,000; and 2,285,000. These Dextran calibration standards are available from American Polymer Standards Corp., Mentor, Ohio. The calibration standards are prepared by dissolving the standards in the mobile phase to make a solution of about 2 mg/ml. The solution sits undisturbed overnight. Then it is gently swirled and filtered through a syringe filter (5 μm Nylon membrane, Spartan-25, available from VWR) using a syringe (5 ml, Norm-Ject, available from VWR).

The starch sample is prepared by first making a mixture of 40 wt % starch in tap water, with heat applied until the mixture gelatinizes. Then 1.55 grams of the gelatinized mixture is added to 22 grams of mobile phase to make a 3 mg/ml solution which is prepared by stirring for 5 minutes, placing the mixture in an oven at 105° C. for one hour, removing the mixture from the oven, and cooling to room temperature. The solution is filtered using the syringe and syringe filter as described above.

The filtered standard or sample solution is taken up by the autosampler to flush out previous test materials in a 100 μl injection loop and inject the present test material into the column. The column is held at 70° C. The sample eluded from the column is measured against the mobile phase background by a differential refractive index detector held at 50° C. and with the sensitivity range set at 64. The mobile phase is DMSO with 0.1% w/v LiBr dissolved therein. The flow rate is set at 1.0 ml/min and in the isocratic mode (i.e., the mobile phase is constant during the run). Each standard or sample is run through the GPC three times and the results are averaged.

The average molecular weight of the high polymer is provided by the material suppliers.

D. Thermal Properties

Thermal properties of the present starch compositions are determined using a TA Instruments DSC-2910 which has been calibrated with an indium metal standard, which has an melting temperature (onset) of 156.6° C. and a heat of melting of 6.80 calories per gram, as reported in the chemical literature. Standard DSC operating procedure per manufacturer's Operating Manual is used. Due to the volatile evolution (e.g., water vapor) from the starch composition during a DSC measurement, a high volume pan equipped with an o-ring seal is used to prevent the escape of volatiles from the sample pan. The sample and an inert reference (typically an empty pan) are heated at the same rate in a controlled environment. When an actual or pseudo phase change occurs in the sample, the DSC instrument measures the heat flow to or from the sample versus that of the inert reference. The instrument is interfaced with a computer for controlling the test parameters (e.g., the heating/cooling rate), and for collecting, calculating and reporting the data.

The sample is weighed into a pan and enclosed with an o-ring and a cap. A typical sample size is 25-65 milligrams. The enclosed pan is placed in the instrument and the computer is programmed for the thermal measurement as follows:

1. equilibrate at 0° C.;
2. hold for 2 minutes at 0° C.;
3. heat at 10° C./min to 120° C.;
4. hold for 2 minutes at 120° C.;
5. cool at 10° C./min to 30° C.;
6. equilibrate at ambient temperature for 24 hours, the sample pan may be removed from the DSC instrument and placed in a controlled environment at 30° C. in this duration;
7. return sample pan to the DSC instrument and equilibrate at 0° C.;
8. hold for 2 minutes;
9. heat at 10° C./min to 120° C.;
10. hold for 2 minutes at 120° C.;
11. cool at 10° C./min to 30° C. and equilibrate; and
12. remove the used sample.

The computer calculates and reports the thermal analysis result as differential heat flow (ΔH) versus temperature or time. Typically the differential heat flow is normalized and reported on per weight basis (i.e, cal/mg). Where the sample exhibits a pseudo phase transition, such as a glass transition, a differential of the ΔH v. time/temperature plot may be employed to more easily determine a glass transition temperature.

E. Water Solubility

A sample composition is made by mixing the components with heat and stirring until a substantially homogeneous mixture is formed. The melt composition is cast into a thin film by spreading it over a Teflon® sheet and cooling at ambient temperature. The film is then dried completely (i.e., no water in the film/composition) in an oven at 100° C. The dried film is then equilibrated to room temperature. The equilibrated film is ground into small pellets.

To determine the % solids in the sample, 2 to 4 grams of the ground sample is placed in a pre-weighed metal pan and the total weight of pan and sample is recorded. The weighed pan and sample is placed in a 100° C. oven for 2 hours., and then taken out and weighed immediately. The % solids is calculated as follows:

$$\% \text{ Solids} = \frac{(\text{dried weight of ground sample \& pan} - \text{weight of pan})}{(\text{first weight of ground sample \& pan} - \text{weight of pan})} \times 100$$

To determine the solubility of the sample composition, weigh 10 grams of ground sample in a 250 mL beaker. Add deionized water to make a total weight of 100 grams. Mix the sample and water on a stir plate for 5 minutes. After stirring, pour at least 2 mL of stirred sample into a centrifuge tube. Centrifuge 1 hour at 20,000 g at 10° C. Take the supernatant of the centrifuged sample and read the refractive index. The % solubility of the sample is calculated as follows:

$$\% \text{ Soluble Solids} = \frac{(\text{Refractive Index \#}) \times 1000}{\% \text{ Solids}}$$

F. Caliper

Prior to testing, the film sample is conditioned at a relative humidity of 48%-50% and at a temperature of 22° C. to 24° C. until a moisture content of about 5% to about 16% is achieved. The moisture content is determined by TGA (Thermo Gravimetric Analysis). For Thermal Gravimetric Analysis, a high resolution TGA2950 Termogravimetric analyzer from TA Instruments is used. Approximately 20 mg of sample is weighed into a TGA pan. Following the manufacturer's instructions, the sample and pan are inserted into the unit and the temperature is increased at a rate of 10° C./minute to 250° C. The % moisture in the sample is determined using the weight lost and the initial weight as follows:

$$\% \text{ Moisture} = \frac{\text{Start Weight} - \text{Weight @ } 250° \text{ C.}}{\text{Start Weight}} \times 100\%$$

Preconditioned samples are cut to a size greater than the size of the foot used to measure the caliper. The foot to be used is a circle with an area of 3.14 square inches.

The sample is placed on a horizontal flat surface and confined between the flat surface and a load foot having a horizontal loading surface, where the load foot loading surface has a circular surface area of about 3.14 square inches and applies a confining pressure of about 15 g/square cm (0.21 psi) to the sample. The caliper is the resulting gap between the flat surface and the load foot loading surface. Such measurements can be obtained on a VIR Electronic Thickness Tester Model II available from Thwing-Albert, Philadelphia, Pa. The caliper measurement is repeated and recorded at least five times. The result is reported in mils.

The sum of the readings recorded from the caliper tests is divided by the number of readings recorded. The result is reported in mils.

EXAMPLES

The materials used in the Examples are as follows:

Crystal Gum® is a modified starch having a weight-average molecular weight of 100,000; Nadex® is a modified starch having a weight average molecular weight of 2,000; and Instant-n Oil® is a modified starch having a weight average molecular weight of 800,000; all are available from National Starch and Chemicals Corp., Bridgewater, N.J.

Superfloc® A-130 is a carboxylated polyacrylamide having a weight-average molecular weight of 12,000,000 to 14,000,000 and is available from Cytec Co., Stamford, Conn.

Nonionic polyacrylamides PAM-a and PAM-b having a weight-average molecular weight of 15,000,000, and 5,000,000 to 6,000,000, respectively, are available from Scientific Polymer Products, Inc., Ontario, N.Y.

Polyethyleneimine having a weight-average molecular weight of 750,000 is available from Aldrich Chemical Co., Milwaukee, Wis.

Parez® 631 NC is a low molecular weight glyoxylated polyacrylamide, and Parez® 802 is a low molecular weight glyoxylated urea resin, both are available from Cytec Co., Stamford, Conn.

Pluronic® F87 is nonionic poloxomer, available form BASF corp., Parsippany, N.J.

Urea, sucrose and glyoxal (in 40% solution in water) are available from Aldrich Chemical Co., Milwaukee, Wis.

Example 1

A melt processable composition of the invention is prepared by mixing 45 wt % starch (Crystal Gum), 40.5 wt % urea, 4.5 wt % sucrose, and 9.8 wt % free water, and manually stirring to form a slurry. Polyacrylamide (PAM-a, Mw=15,000,000) is dissolved in water to form a PAM aqueous solution. An aliquot of the polymer/water solution is added to the slurry. Water in the slurry is then evaporated until the weight percent of polyacrylamide in the final mixture is 0.2 wt %.

The composition has a shear viscosity of 0.65 Pa·s and an extensional viscosity of 1863.2 Pa·s, at $700s^{-1}$ and 90° C.

Comparative Example 1b

A comparative starch composition is prepared according to Example 1 except no polyacrylamide is added to the composition. The composition has a shear viscosity of 1.35 Pa·s and an extensional viscosity of 43.02 Pa·s, at $700s^{-1}$ and 90° C. Example 1 and Comparative Example 1b demonstrate that addition of a small amount of high polymer decreases the shear viscosity slightly and significantly increases the extensional viscosity.

Example 2

A melt processable composition of the invention is prepared by mixing 50wt % starch (Crystal Gum), 30 wt % urea, 1.5 wt % sucrose, and 18.5 wt % free water, and manually stirring to form a slurry. Polyacrylamide (Superfloc A-130, Mw=12-14,000,000) is dissolved in water to form a PAM aqueous solution. An aliquot of the polymer/water solution is added to the slurry. Water in the slurry is then evaporated until the weight percent of polyacrylamide in the final mixture is 0.003 wt %.

The composition has a shear viscosity of 1.12 Pa·s and an extensional viscosity of 46.0 Pa·s, at $700s^{-1}$ and 90° C.

Comparative Example 2b

A comparative starch composition is prepared according to Example 2 except no polyacrylamide is added to the composition. The composition has a shear viscosity of 1.23 Pa·s and an extensional viscosity of 0.69 Pa·s, at $700s^{-1}$ and 90° C. Example 2 and Comparative Example 2b demonstrate that addition of a small amount of high polymer decreases the shear viscosity slightly and significantly increases the extensional viscosity.

Example 3

A torque rheometer having a melt blowing die is used to process the composition of Example 1. The torque rheometer is illustrated in FIG. 1. The torque rheometer assembly 100 includes a drive unit 110 (Model Rheocord 90 available from Haake GmbH), a barrel 120 partitioned into four temperature zones 122, 124, 126 and 128, a feed port 121, and a melt spinning die assembly 130. Twin screw elements 160 (model TW100, from Haake GmbH) are attached to the drive unit 110 and disposed within the barrel 120. A six inch wide melt blowing die assembly 130 (available from JM Laboratories, Dawsonville, Ga.) is connected to the end of the barrel via a pump 140. The die assembly has a spinneret plate which has 52 holes per linear inch and a hole diameter of 0.015" (0.0381 cm), surrounded by a 0.02" wide air passageway 152, from which a high velocity air stream 150 impinges the extruded filaments just below the spinneret plate. The air stream has the effect of simultaneously blowing the filaments away from the spinneret and attenuating the filaments.

The composition of is prepared (as described in Example 1) by mixing 45 wt % starch (Crystal Gum), 0.2 wt % polyacrylamide (PAM-a), 40.5 wt % urea, 4.5 wt % sucrose, and 9.8 wt % water. The mixture is gravity-fed via feed port 121 into a torque rheometer. The torque rheometer and die assembly are set as follows:

| Barrel Temperature | |
| --- | --- |
| Zone 122 | 70° C. |
| Zone 124 | 90° C. |
| Zone 126 | 90° C. |
| Zone 128 | 90° C. |
| Torque | 100 rpm |
| Die Temperature | 126.7° C. |
| Air Temperature | 126.7° C. |
| Air Pressure | 35 psi |
| Pump | 40 rpm |

The mixture is conveyed from the extruder through the pump into the melt blowing die. The resulting attenuated filaments (or fine fibers) of the invention have fiber diameters ranging from 8 to 40 microns.

Note that the weight percent starch in the melt processable composition includes the weight of starch and the weight of bound water (which is on the average about 8 wt % of the starch). It is to be understood that the as-prepared compositions are used for uniaxial and biaxial extensional processes. However, most of the water is lost during the melt process, and the resulting starch fiber, film or like product contains little or no free water. The resulting product does contain some bound water (possible by absorbing moisture from ambient environment). Therefore, the composition of the resulting product may be more appropriately expressed by its solid components, calculated on a dry solid basis. For example, to calculate, on a dry solid basis, the composition of the fiber made according to Example 3, one would take out the 9.8 wt % free water from the overall composition and the 8 wt % bound water from the starch, then normalize the remaining solid content to 100%. Thus, the composition of the fiber of Example 3 calculated on a dry solid basis would be 47.8 wt % starch solid (without bound water), 0.23 wt % polyacrylamide, 46.8 wt % urea and 5.2 wt % sucrose.

Example 4

Figure 3A:
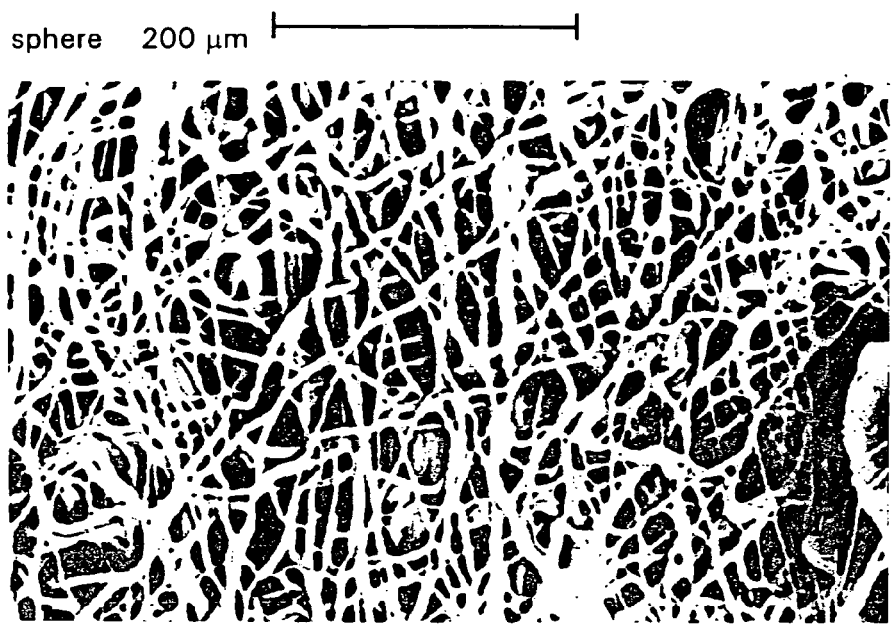
FIG. 3a is the Scanning Electron Micrographs of fine starch fibers of the present invention shown on a 200 micron scale.
Figure 3B:
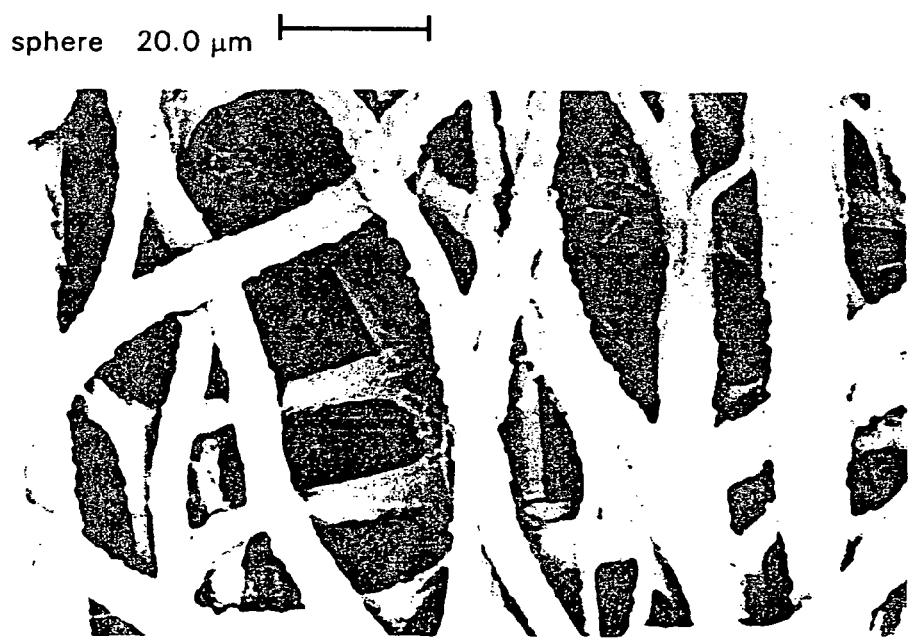
FIG. 3b is the Scanning Electron Micrographs of fine starch fibers of the present invention shown on a 20 micron scale.

The composition of Example 2 is melt blown into fine fibers of the invention. FIG. 3a is the Scanning Electron Micrographs of fine starch fibers made from the composition of Example 2 using the process described in Example 3, shown on a 200 micron scale. FIG. 3b is the Scanning Electron Micrographs of the same starch fibers shown on a 20 micron scale. Both figures show that starch fibers of Example 4 have a fairly consistent fiber diameter of about 5 microns.

Example 5

Fifteen grams of starch (Crystal Gum, Mw=100,000) and fifteen grams of free water are mixed together at 80° C. with manual stirring until the mixture becomes substantially homogeneous or gelatinizes. A high polymer (PAM-a, Mw=15,000,000) is dissolved in free water to form a PAM aqueous solution of known concentration. An aliquot of the polymer/water solution is added to the starch/water mixture such that the overall mixture contains 0.006 grams of PAM-a. Then the overall mixture is heated to evaporate water until the weight of the final mixture (starch, PAM-a and water) equals 30 grams. This mixture is subjectively shown to have suitable melt extensibility for drawing fibers.

Examples 6-8

Mixtures of starch (Crystal Gum), high polymer and water are prepared in the same manner as in Example 5. The final compositions of these mixture are shown below.

| | | Mw | | Ex-6 | Ex-7 | Ex-8 |
| --- | --- | --- | --- | --- | --- | --- |
| Starch | Crystal Gum | 100,000 | wt % | 49.99 | 49.99 | 46.92 |
| Polyacrylamide | Superfloc A-130 | 12-14,000,000 | wt % | 0.02 | | |
| | PAM-b | 5-6,000,000 | wt % | | 0.02 | |
| Polyethyleneimine | | 750,000 | wt % | | | 6.17 |
| Water | | | wt % | 49.99 | 49.99 | 46.91 |

These compositions of the invention are subjectively shown to have suitable melt extensibility for drawing fibers.

Examples 9-11

The following compositions are prepared in the same manner as Example 1.

|  |  | Mw |  | Ex-9 | Ex-10 | Ex-11 |
|---|---|---|---|---|---|---|
| Starch | Crystal Gum | 100,000 | wt % | 41.54 | 20.77 | 20.77 |
|  | Nadex | 2,000 | wt % |  | 20.77 |  |
|  | Instant-n Oil | 800,000 | wt % |  |  | 20.77 |
| Polyacrylamide | PAM-a | 15,000,000 | wt % | 0.08 | 0.08 | 0.08 |
| Urea |  |  | wt % | 6.23 | 6.23 | 6.23 |
| Sucrose |  |  | wt % | 6.23 | 6.23 | 6.23 |
| Parez 631 NC |  |  | wt % | 1.04 | 1.04 | 1.04 |
| Water |  |  | wt % | 44.88 | 44.88 | 44.88 |

These compositions of the invention are expected to have suitable melt extensibility for drawing fibers. And where the water has been adjusted to about pH 2, the resulting fibers are expected to have a water solubility of less than 30%, based on the test method disclosed herein.

Example 12

A melt processable composition is prepared by mixing 45 wt % starch (Crystal Gum), 0.2 wt % polyacrylamide (PAM-a), 40.5 wt % urea, 4.5 wt % sucrose, and 9.8 wt % water to form a slurry. The composition is melt blown into fine fibers using a torque rheometer as shown in FIG. 1 in the manner described in Example 3, except the mixture is meter-fed into the torque rheometer. The torque rheometer and die assembly are set as follows:

| Barrel Temperature |  |
|---|---|
| Zone 122 | 70° C. |
| Zone 124 | 90° C. |
| Zone 126 | 90° C. |
| Zone 128 | 90° C. |
| Torque | 140 rpm |
| Feed Rate | 16 gm/min |
| Die Temperature | 137.8° C. |
| Air Temperature | 137.8° C. |
| Air Pressure | 50 psi |
| Pump | 40 rpm |

The resulting attenuated filaments (or fine fibers) of the invention have fiber diameters ranging from 10 to 30 microns. The fibers are air laid onto a papermaking forming fabric as described in U.S. Pat. No. 4,637,859, with the fabrics of U.S. Pat. Nos. 5,857,498, 5,672,248, 5,211,815 and 5,098,519, all incorporated herein by reference, also being judged suitable for this purpose.

Example 13

The resultant web from the air-laying process of Example 12 is tested for oil absorbency. A drop of a commercially available motor oil (SAE 20 grade, by the Society of Automobile Engineers' designation) is placed on the web and on a commercially available paper towel, respectively, for comparison of oil absorbency. The web shows an improved oil absorbency over that of the commercial paper towel in the following aspects: (1) the web absorbs oil faster than the commercial paper towel, as shown by a shorter residence time on the surface of the web; and (2) after 30 seconds, the web has a spot size of about 1.5 to 2 times larger in diameter than that of the commercial paper towel.

Example 14

This example illustrates that the starch composition of the present invention can be made into building materials, e.g., pressed board. A melt processable composition is prepared by mixing 60 wt % starch (Crystal Gum), 0.1 wt % polyacrylamide (SP2), 2 wt % urea, 2 wt % sucrose, 1.5 wt % Parez 631 NC and 34.4 wt % water (adjusted to pH 2 with sulfuric acid) to form a slurry. The slurry is fed in to a torque rheometer (Model Rheocord 90) as illustrated in FIG. 1 and operated under the conditions as described in Example 12 above, except a single capillary die (having a 1 mm diameter and a temperature of 90° C.) is used instead of a melt spinning die. The extruded strand is dusted with saw dust or wood shavings while still wet and sticky. The dusted strands are compressed together to form a log. The log is dried at 40° C. in a forced air oven for two hours to get rid of the residual water from the starch composition. The final product is a log of 47.8 wt % saw dust and 52.2 wt % dried starch composition.

Example 15

This example illustrates that the present invention can be incorporated into structural materials as reinforcements. Though this example uses fibers made from a composition without high polymers. It is believed that when a composition of the present invention is used, the product would show better or equivalent performances.

A comparative cement sample is prepared as follows: 5 parts of commercially available Quikrete Anchoring cement are mixed with 1.5 part clean tap water until a thick syrup consistency is obtained. Within 5 minutes of mixing, the cement was introduced into cylindrical molds in order to obtain a constant dimension sample for evaluation. Thin wall molds 5" long and 0.23" in inner diameter (i.e., commercially available straws) are filled by driving the pasty cement mixture up from the bottom. This filling method eliminates air inclusion in the finished sample. The samples are allowed to cure for 5 days prior to evaluation. The mold is carefully scored on the outer surface so as not to damage the sample inside, then the mold is peeled away to retrieve the comparative sample (Example 15b).

A melt processable composition is prepared by mixing 45 wt % starch (Durabond®, available from National Starch and Chemicals Corp., Bridgewater, N.J.), 15 wt % urea, 15 wt % sorbitol, and 25 wt % water to form a slurry. The slurry is fed in to a torque rheometer (Model Rheocord 90) as illustrated in FIG. 1 and operated under the condition as described in Example 14 above. The fibers are about 0.02" in diameter and are cut to 1" in length for use herein. The extruded, thin spaghetti-like strands are incorporated into cement as follows: 5 parts of commercially available Quikrete Anchoring cement are mixed with 1.5 part clean tap water and 0.5% (on a dry weight basis) starch fibers. The additional amount of water added herein is required to achieve the comparable consistency as the comparative sample above. The sample molds are filled and the samples (Example 15) are cured and retrieved in the same manner as above.

The samples are subjectively evaluated by bending to failure by hand. Example 15 are subjectively judged to be slightly weaker than the comparative Example 15b. Example 15 has an apparent density of 1.46 g/linear inch while comparative Example 15b has an apparent density of 1.48 g/linear inch. Therefore, it is demonstrated that Example 15 offers the benefits of light weight and lower cost (on a volume basis).

Example 16

This example illustrates that the composition of the present invention can prophetically be made into a controlled water release material when mixed with potting soil. The controlled water release is useful for horticultural and agricultural plants which thrive in a relatively low humidity environment and/or infrequent watering. A melt processable composition is prepared by mixing 50 wt % starch (Durabond®, available from National Starch and Chemicals Corp., Bridgewater, N.J.), 0.1 wt % polyacrylamide (SP2®), 15 wt % urea, 15 wt % sorbitol, 1.5 wt % Parez® and 18.4 wt % water to form a slurry. The slurry is fed in to a torque rheometer (Model Rheocord 90) as illustrated in FIG. 1 and operated under the condition as described in Example 14 above. The extruded, thin spaghetti-like strands are allowed to dry before mixing with potting soil. The ratio of starch-based strand to potting soil depends on the requirements of various types of plants. Generally, 10 wt % of starch-based strands in potting soil shows satisfactory water holding/release results.

Examples 17-19

Examples 17-19 use films made from compositions without the benefit of high polymers. It is believed that when a composition of the present invention is used in each of these examples, the resultant product would show beneficial improvements in properties, e.g., lower caliper, greater flexibility.

Example 17

This example illustrates that the compositions of the invention can be made into thin films, using a Werner & Pfleiderer ZSK-30 co-rotating twin-screw extruder with a L/D ratio of 40. The screw configuration consists of four kneading sections and five conveying sections. The extruder barrel consisted of an unheated feed zone followed by seven heated zones, which are designated consecutively as Zones A, B, 1, 2, 3, 4 and 5. The barrel is controlled to the temperature profile summarized below, and the screw speed is set to 150 rpm.

| | Zone | | | | | | |
|---|---|---|---|---|---|---|---|
| | A | B | 1 | 2 | 3 | 4 | 5 |
| Temperature ° C. | 50 | 50 | 50 | 95 | 95 | 95 | 95 |

A melt processable composition is prepared by metering the solid materials into the extruder with a K2V-T20 volumetric feeder (available from K-Tron Inc., Pitman, N.J.) and metering the liquid material into Zone 1 of the extruder with a mini pump (available from Milton-Roy, Ivyland, Pa.). The components are: 44 wt % starch (Durabond® A, available from National Starch and Chemicals Corp., Bridgewater, N.J.), 18 wt % urea, 18 wt % sucrose, and 20 wt % water. The mixture is conveyed from the extruder into a Zenith B-9000 gear pump into a six-inch wide flat film die (available from Killion Extruders, Cedar Grove, N.J.) at a flow rate of 33 $cm^3$/min, wherein the gear pump is maintained at 96° C., the film die is maintained at 94° C. and the die opening is set at 15 mils. The resultant film is extruded onto a 12-inch wide chill roll (available from Killion Extruders) which is maintained at 37° C. The film is then wound onto a paper core at a speed of 5 fpm. The resultant film is about 1 mil in thickness, slightly tacky to the touch, and exhibits excellent flexibility (i.e., it can be repeatedly bent at a 180 degree angle without breaking or forming a dead fold).

Example 18

This example illustrates that the film from Example 17 can be made into a seed carrier for agricultural applications. The seed carrier film made according to this example provides an inexpensive material that can be laid down to cover and seed a large area effectively. The material holds water to facilitate the germination of the seeds, and the material is biodegradable such that no recovery and disposal are required. The film of Example 17 is placed on a single-sided release paper and sprinkled with grass seeds available from Midwestern Supply or other garden supply stores. Another sheet of single-sided release paper is placed on top of the seeds. The assembly is placed between ¼ inch (0.635 cm) aluminum plates and inserted into a 6 inch by 6 inch (15.24 cm by 15.24 cm) Carver hot press that is preheated to 207° C. The assembly is equilibrated under low/contact pressure for one minute, then pressure is increased to a maximum pressure of 6000 pounds. The assembly is held under the maximum pressure for one minute and quickly depressurized. The assembly is taken out of the press and cooled to room temperature. The resulting film composite shows good cohesion between film and seeds such that the film composite can be handled without loss of seeds.

Example 19

This example illustrates that the films of Example 17 are fusable such that the films can be made into substantially transparent bags/pouches useful as sealable food storage pouches, shopping bags, garbage bags, grocery bags, and the like. Two pieces of 4 inch by 4 inch (10.16 cm by 10.16 cm) films are overlaid with a piece of release paper interposed between them. The release paper should be smaller than the films so that at least three edges of the films are in direct contact with each other. A Vertrod impulse sealer (Model 24LAB-SP) is used to seal three sides of the overlaid films. The sealer is set at 50% voltage, 60 psi pressure, a six second dwell time (one second on and 5 seconds off), and for a total sealing time of one minute. The resultant bag shows uniform, welded seals on three sides. The fourth side can optional be sealed to form a completely sealed pouch.

Example 20

This example illustrates the water-insoluble starch compositions of the present invention. A composition is prepared by mixing 50 wt % starch (Crystal Gum), a crosslinking additive (the type and the amount of the crosslinking additive are shown in the Table below) and a balance of water which has been adjusted to pH 2 using sulfuric acid. Where glyoxal (in 40% solution in water) is used, there is no need to adjust the water pH. The composition and test sample are prepared according to Test Method for Water Solubility described hereinabove. The results are shown in the Table below:

| | Solubility: | | |
|---|---|---|---|
| % Additive | Parez 631 | Glyoxal | Parez 802 |
| 0.00% | 37% | 37% | 37% |
| 0.12% | | 16% | |
| 0.20% | | 10% | |
| 0.25% | 28% | | 48% |
| 0.32% | | 11% | |
| 0.40% | | 7% | |
| 0.50% | 16% | | 16% |
| 0.75% | 14% | | 9% |
| 1.00% | 14% | | 6% |
| 1.50% | 11% | | 4% |

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. A composition comprising:
   (a) from about 50 wt % to about 70 wt % of a starch, wherein the starch has a weight-average molecular weight ranging from about 1,000 to about 2,000,000; and
   (b) from about 30 wt % to about 50 wt % of water; and
   (c) a high polymer selected from the group consisting of: polyacrylamide and its derivatives; polyacrylic acid, polymethacrylic acid, and their esters; polyvinyl alcohol; polyethyleneimine; copolymers made from mixtures of monomers of the aforementioned polymer; and mixtures thereof;
   wherein the composition has a melt shear viscosity in the range of about 0.1 to about 40 Pa·s.

2. The composition of claim 1 wherein from about 20 to about 99 wt % of the starch is amylopectin.

3. The composition of claim 1 wherein the weight-average molecular weight of the starch ranges from about 1,500 to about 800,000.

4. The composition of claim 1 wherein the composition further comprises a plasticizer.

5. The composition of claim 4 wherein the plasticizer comprises a hydroxyl plasticizer.

6. The composition of claim 1 wherein the weight-average molecular weight of the high polymer ranges from about 800,000 to about 22,000,000.

7. The composition of claim 1 wherein a solubility parameter of the high polymer and a solubility parameter of starch differ by less than 10 MPa$^{1/2}$.

8. The composition of claim 1 wherein the composition further comprises at least one additive selected from the group consisting of oxidation agents, cross-linking agents, emulsifiers, surfactants, debonding agents, lubricants, processing aids, optical brighteners, antioxidants, flame retardants, dyes, pigments, fillers, proteins and their alkali salts, biodegradable synthetic polymers, waxes, low melting synthetic thermoplastic polymers, tacktifying resins, extenders, wet strength resins, and mixtures thereof.

9. The composition of claim 1 wherein the weight-average molecular weight of the starch ranges from about 1,500 to about 800,000, the weight average molecular weight of the high polymer ranges from about 800,000 to about 22,000,000, and the solubility parameter of the high polymer and the solubility parameter of the starch differ by 10 MPa$^{1/2}$.

10. The composition of claim 1 wherein the composition further comprises a polar solvent selected from the group consisting of: $C_1$-$C_{18}$ linear or branched alcohols, dimethyl sulphoxide, formamide and derivatives thereof, acetamide and derivatives thereof, glycol alkyl ether and derivatives thereof, hydrazine, ammonia and mixtures thereof.

11. A process for preparing a composition, the process comprising the steps of:
   (a) providing from about 50 wt % to about 70 wt % of a starch having a weight-average molecular weight from about 1,000 to about 2,000,000;
   (b) providing from about 30 wt % to about 50 wt % of water and
   (c) a high polymer selected from the group consisting of: polyacrylamide and its derivatives; polyacrylic acid, polymethacrylic acid, and their esters; polyvinyl alcohol; polyethyleneimine; copolymers made from mixtures of monomers of the aforementioned polymer; and mixtures thereof;
   (d) mixing the starch, water and high polymer together to form a composition having a melt shear viscosity in the range of about 0.1 to about 40 Pa·s.

12. The process according to claim 11 wherein the step (d) comprises the steps of feeding the starch and the water into an extruder, and extruding a mixture thereof.

13. A composition comprising from about 50 wt % to about 70 wt % of a starch, from about 30 wt % to about 50 wt % of water and a high polymer selected from the group consisting of: polyacrylamide and its derivatives; polyacrylic acid, polymethacrylic acid, and their esters; polyvinyl alcohol; polyethyleneimine; copolymers made from mixtures of monomers of the aforementioned polymer; and mixtures thereof; wherein the composition has:
   (a) a melt shear viscosity of less than about 50 Pa·s; and
   (b) an extensional viscosity, which is at least 10 times greater than that of a comparative composition having no high polymer therein.

14. The composition of claim 13 wherein the composition has an uniaxial draw ratio ranging from about 5 to about 6000.

15. The composition of claim 13 wherein the composition has a melting temperature ranging from about 80° C. to about 180° C.

* * * * *